(12) United States Patent
Ogawa

(10) Patent No.: US 7,988,665 B2
(45) Date of Patent: Aug. 2, 2011

(54) INFUSION FLUID HEATING APPARATUS

(76) Inventor: Genshirou Ogawa, Inuyama (JP)

(*) Notice: Subject to any disclaimer, the term of this patent is extended or adjusted under 35 U.S.C. 154(b) by 269 days.

(21) Appl. No.: 12/226,859

(22) PCT Filed: May 10, 2006

(86) PCT No.: PCT/JP2006/309430
§ 371 (c)(1),
(2), (4) Date: Oct. 30, 2008

(87) PCT Pub. No.: WO2007/129412
PCT Pub. Date: Nov. 15, 2007

(65) Prior Publication Data
US 2009/0082726 A1    Mar. 26, 2009

(51) Int. Cl.
*A61F 7/12* (2006.01)
*A61F 7/00* (2006.01)
*A61M 37/00* (2006.01)

(52) U.S. Cl. .................. 604/113; 604/6.13; 604/291

(58) Field of Classification Search .......... 604/113–114, 604/291, 6.13; 600/555; 606/22
See application file for complete search history.

(56) References Cited

U.S. PATENT DOCUMENTS

| | | | |
|---|---|---|---|
| 4,293,762 A * | 10/1981 | Ogawa | 392/470 |
| 4,309,592 A * | 1/1982 | Le Boeuf | 392/470 |
| 4,680,445 A | 7/1987 | Ogawa | |
| 4,709,135 A | 11/1987 | Dietrich et al. | |
| 7,715,700 B2 | 5/2010 | Ogawa | |
| 2002/0081109 A1 * | 6/2002 | Mitsunaga et al. | 392/470 |
| 2003/0114795 A1 * | 6/2003 | Faries et al. | 604/113 |

FOREIGN PATENT DOCUMENTS

| | | |
|---|---|---|
| DE | 3606930 A1 | 9/1987 |
| JP | B2-58-30056 | 6/1983 |
| JP | A-1-259871 | 10/1989 |
| JP | A-2000-502938 | 3/2000 |
| JP | A-2002-102349 | 4/2002 |
| WO | WO 2005/077436 A1 | 8/2005 |

OTHER PUBLICATIONS

Oct. 8, 2010 Chinese Office Action issued in Chinese Patent Application No. 200680054919.2 (with partial translation).
Nov. 8, 2010 Supplementary European Search Report for European Patent Application No. 06746240.8.

* cited by examiner

*Primary Examiner* — Nicholas D Lucchesi
*Assistant Examiner* — Rebecca E Eisenberg
(74) *Attorney, Agent, or Firm* — Oliff & Berridge, PLC

(57) ABSTRACT

An infusion fluid heating apparatus applicable to various types of infusion tube with different length dimensions includes a front-side tube fitting groove or a rear-side tube fitting groove formed on one of surfaces of a heating plate that receives an infusion tube in a first length between an inlet opening and an outlet opening open at the end surfaces of the heating plate. The groove also receives the infusion tube in a second length shorter than the first length. Therefore, the groove uses the second length for a relatively short infusion tube, capable of heating the tube appropriately and achieving high versatility. In addition, the tube fitting groove uses the first length for an infusion bag with a relatively long infusion tube, capable of heating the tube appropriately and increasing the maximum infusion fluid flow.

12 Claims, 8 Drawing Sheets

INFUSION FLUID HEATING APPARATUS

TECHNICAL FIELD

The prevent invention relates to improvement of an infusion fluid heating apparatus for pre-heating infusion fluid up to a suitable temperature, when introducing the infusion fluid into a living body mainly in a medical field.

BACKGROUND ART

In actual medical field, an infusion fluid such as blood, a nutrition liquid, a liquid medicine is occasionally introduced into a living body. In such a case, in general, the fluid is packed in an infusion bag or bottle hung on a stand, and is injected into a blood vessel of a living body, etc. through a drip tube, a roller clamp, an infusion tube, and an injection needle connected thereto.

Such infusion fluid is often stored at a relatively low temperature in response to the requirement of quality preservation. Accordingly, for example, when infusion is needed in emergency surgery, etc., the infusion fluid may be required to be heated up to around the living body temperature as quickly as possible. For this reason, infusion fluid heating apparatuses have been developed, which pre-heats the fluid up to a suitable temperature in the process of introducing an infusion fluid as described above. Examples thereof include infusion fluid heating apparatuses described Patent Publications 1 and 2. The infusion fluid heating apparatuses comprise, for example, a heating plate formed on one surface thereof a tube fitting groove which receives the above-mentioned infusion tube, and an electrical heater for imparting heat energy to the plate. The above-mentioned electrical heater is operated with the infusion tube being fitted into the tube fitting groove formed on one surface of the heating plate, thereby heating the fluid which circulates through the infusion tube.

Patent Publication 1: JP2002-102349A
Patent Publication 2: JP2000-502938A

DISCLOSURE OF THE INVENTION

In general, in an infusion fluid heating apparatus, the longer the portion of an infusion tube used for heating, the greater the maximum flow of the infusion fluid. Accordingly, larger heating length is preferable. However, the infusion tube length between an infusion bag containing an infusion fluid and a drip tube or a roller clamp differs for every standard or regulation. Consequently, in order to improve versatility, the heating length of a heating plate has to be small to heat a short infusion tube, which causes a disadvantage of a limited maximum flow when the plate is used for a long infusion tube.

The invention was accomplished against the above background, and has an object to provide an infusion fluid heating apparatus which is versatile enough to be applicable to various infusion tubes with different length dimensions, and which can also increases the maximum infusion fluid flow amount for an infusion bag with a long infusion tube.

For achieving the above object, the present invention relates to an infusion fluid heating apparatus, having a heating plate formed on one surface thereof a tube fitting groove receiving a infusion tube, for pre-heating an infusion fluid to be supplied to a living body through the infusion tube to a preset temperature. The infusion fluid heating apparatus is characterized by that the tube fitting groove formed on one surface of the heating plate receives the infusion tube in a first length between an inlet opening and an outlet opening both opened at an end surface of the heating plate, and also receives the infusion tube in a second length shorter than the first length.

As described above, the tube fitting groove formed on one surface of the heating plate receives the infusion tube in a first length between the inlet opening and the outlet opening both opened at the end surfaces of the heating plate, and also receives the infusion tube in a second length which is shorter than the first length. Therefore, the tube fitting groove uses the second length for a relatively short infusion tube, capable of heating the tube appropriately and achieving high versatility. In addition, the tube fitting groove uses the first length for an infusion bag with a long infusion tube, capable of heating the tube appropriately and increasing the maximum infusion fluid flow amount.

Preferably, the tube fitting groove of the heating plate includes a basic groove formed in the first length between the inlet opening and the outlet opening, and a shunting groove shunting the basic groove in a middle thereof so that the second length is defined between the inlet opening and the outlet opening. This enables the application of a part of the basic groove to both cases of the first length of the infusion tube being inserted and where the second length of the infusion tube being inserted. Thus, size of the heating plate is made compact.

Further, preferably, the infusion fluid heating apparatus further comprises a case to which the heating plate is detachably attached. The heating plate in formed on other surface thereof a second tube fitting groove having a different sectional shape from the tube fitting groove formed on the one surface. This enables heating of the infusion tubes with different sectional shapes or diameter dimensions, thereby further improving versatility.

Further, preferably, the second tube fitting groove receives the infusion tube in a third length between an inlet opening and an outlet opening both opened at the end surface of the heating plate, and also receives the infusion tube in a third length which is shorter than the first length. As a result, on the other surface of the heating plate, the groove can use the fourth length for a relatively short infusion tube, making is possible to heat the tube appropriately and achieve high versatility. Additionally, the groove can use the third length for an infusion bag with a long infusion tube, making is possible to heat the tube appropriately and increase the maximum infusion fluid flow, thereby achieving higher versatility.

Further, preferably, the case contains an electrical heater closely fit to the heating plate, a temperature sensor directly or indirectly detecting a temperature of the infusion fluid in the infusion tube near the outlet opening, and a control unit controlling a heat generation amount of the electrical heater so that the temperature detected by the temperature sensor coincides with a preset target temperature. This enables any various type of infusion fluid in an infusion bag to be introduced at a constant preset temperature.

Further, preferably, the case is provided with an infusion bag containing the infusion fluid, in place of the heating plate. This enables heating of an infusion fluid even if the infusion tube is extremely short, provided that the volume of the bag is relatively small.

EXPLANATION OF REFERENCE NUMERALS

| | |
|---|---|
| 10: infusion fluid heating apparatus | 12: case body |
| 20: case | 32: temperature control unit |
| 38: electrical heater | 40: heating plate |
| 50: front-side tube fitting groove | 52, 62: inlet opening |
| 54, 64: outlet opening | 60: rear-side tube fitting groove |
| 66: basic groove | 68a: shunting groove |
| B: infusion bag | TU: infusion tube |

BEST MODES FOR CARRYING OUT THE INVENTION

Hereinafter, one preferred embodiment of the invention will be explained in detail based on the drawings.

Embodiment

Figure 1:
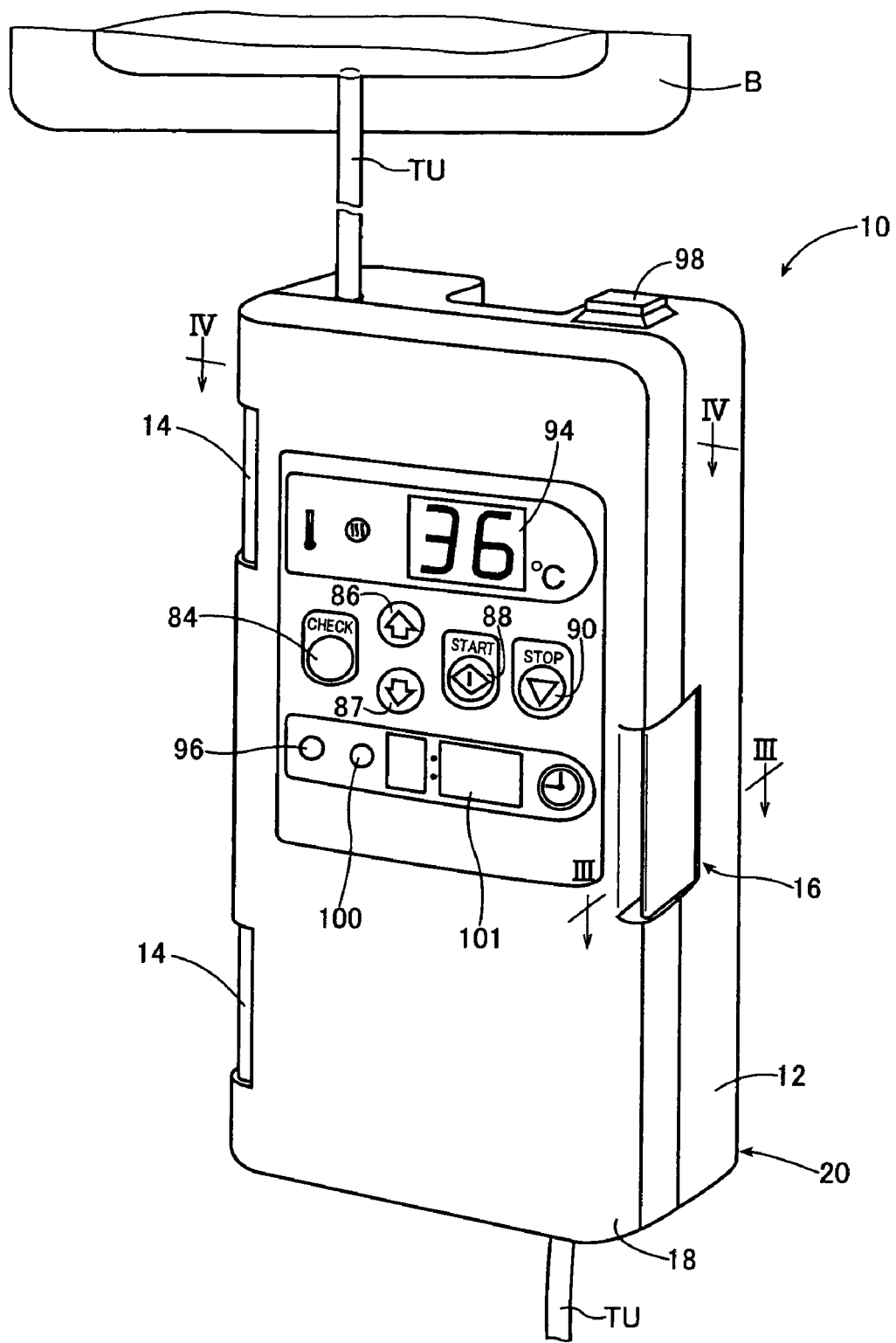
FIG. 1 is a perspective view showing an infusion fluid heating apparatus which is a first embodiment of the invention.
Figure 2:
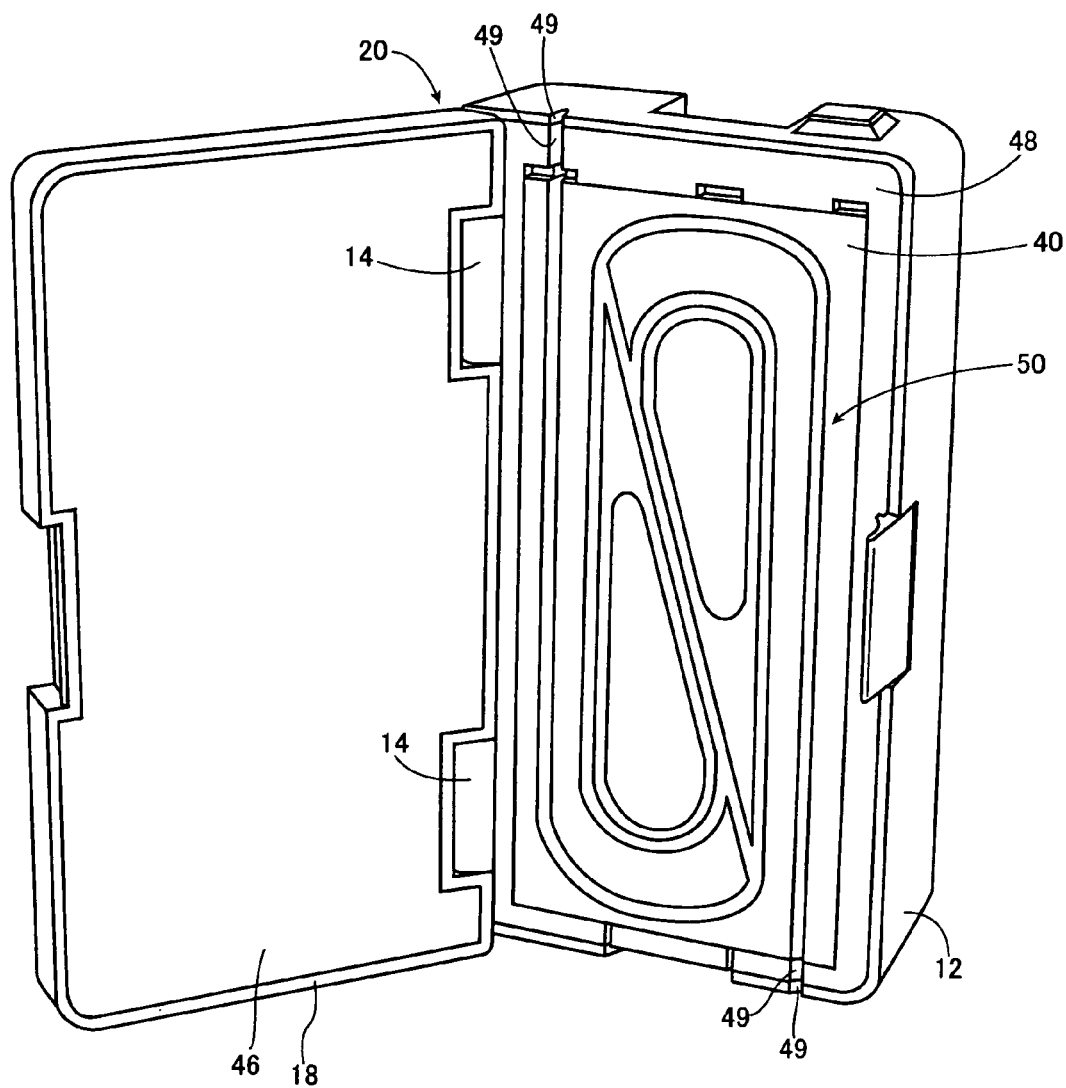
FIG. 2 is a perspective view of the infusion fluid heating apparatus shown in FIG. 1 with its lid open.

FIG. 1 is a perspective view illustrating structure of an infusion fluid heating apparatus 10 which is a first embodiment of the invention, and FIG. 2 is a perspective view thereof with the lid thereof open. As shown in these figures, the infusion fluid heating apparatus 10 includes a case 20 having a case body 12 and a lid 18. The case body 12 is made of a synthetic resin, and forms a rectangular parallelepiped-shaped housing with one face open. The lid 18 is pivotally attached via a pair of hinges 14 to one of paired long sides forming a part of the rectangular opening edge of the case body 12. The lid 18 is locked with a locking device 16 made of a synthetic resin and provided in a longitudinal center of other long side. The lid 18 has a thickness (depth) smaller than that of the case body 12, but also forms a rectangular parallelepiped-shaped housing with its opposite face to the case body 12 being open. The lid 18 is connected to the case body 12 via the pair of hinges 14 provided at one of paired long sides forming a part of the opening edge of its rectangular shape.

Figure 3:
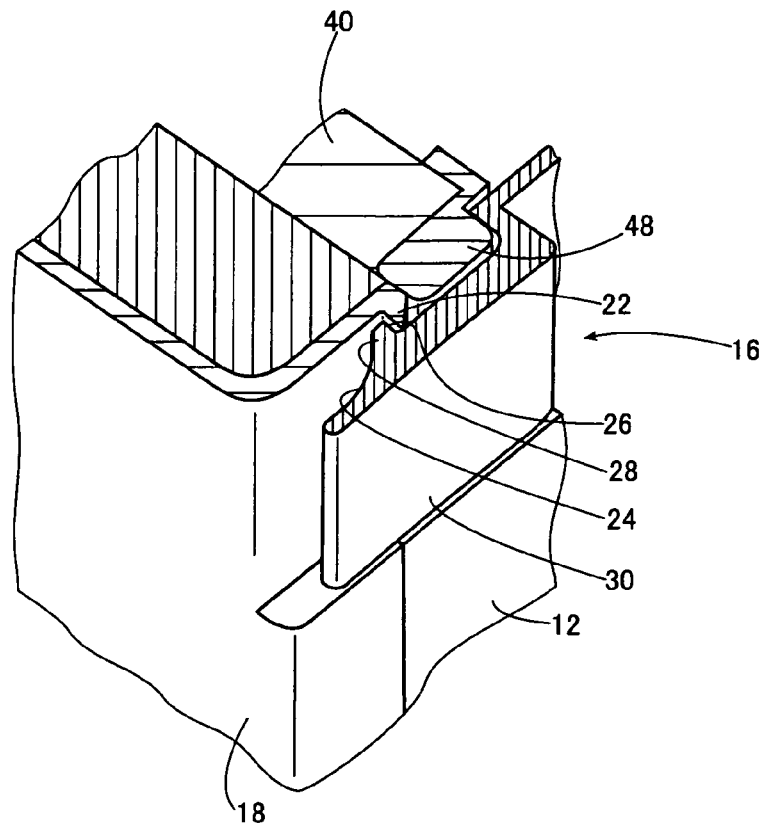
FIG. 3 is III-III sectional view of FIG. 1, enlarged to illustrate structure of a locking device which fixes a lid of the infusion fluid heating apparatus shown in FIG. 1.

As shown in FIG. 3, the locking device 16 includes a locking projecting portion 22 and an unlocking operation unit 30. The locking projecting portion 22 is integrally formed in the center of the other long side of the paired long sides forming a part of the opening edge of the rectangular shape of the lid 18, to project approximately by the height corresponding to its thickness in a direction away from the hinges 14, i.e., in the thickness direction. The longitudinal unlocking operation unit 30 is integrally formed so as to project from the surface of the case body 12 toward the lid 18. The longitudinal unlocking operation unit 30 has a locking projection 28 defined by a slope 24 formed on an internal side surface so that the thickness increases in a direction away from the front end, and an engaging surface 26 which is continuous to the slope 24 and is formed in a direction perpendicularly in the longitudinal direction.

Accordingly, in the process of closing the lid 18, the locking projecting portion 22 first slidingly contacts with the slope 24 to thereby press up the unlocking operation unit 30. Subsequently, as the locking projecting portion 22 passes the locking projection 28, the lid 18 returns to its original position due to an elastic recovery of the unlocking operation unit 30, to engages with the engaging surface 26 of the unlocking operation unit 30. Thus, the lid 18 is closed and fixed. When the unlocking operation unit 30 is manually operated in a direction away from the lid 18, the engaging surface 26 of the unlocking operation unit 30 is disengaged from the locking projecting portion 22. Thus, the lid 18 is manually opened.

Figure 4:
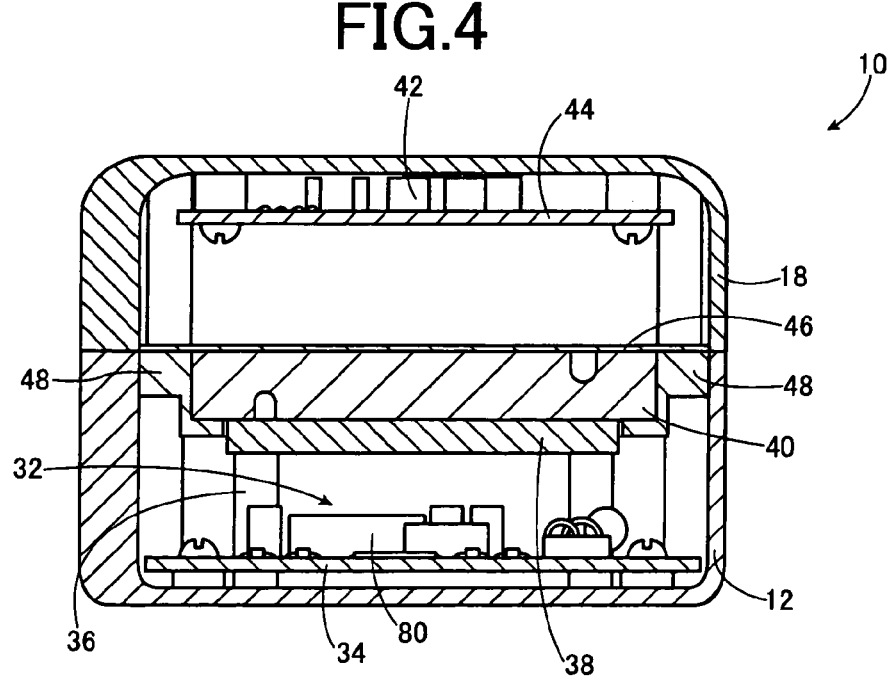
FIG. 4 is IV-IV cross sectional view of FIG. 1, illustrating the structure of the infusion fluid heating apparatus shown in FIG. 1.

As shown in the sectional view in FIG. 4, in the case body 12, a first circuit substrate 34 provided with a temperature control unit 32 is fixed, and an electrical heater 38 is also fixed via a spacer 36. At the opening of the case body 12, a rectangular frame-shaped frame member 48 is fixed, which allows the rectangular heating plate 40 to be inserted detachably in a flush manner in close contact with i.e. close fitting to the electrical heater 38. In the lid 18, a second circuit substrate 44 provided with a display 42 is fixed. At the opening edge of the lid 18, a plate member 46 is fixed, which covers the opening of the lid 18 and closely contacts with the surface of the heating plate 40. The case body 12 and the frame member 48 disposed therein are each provided with a notch groove 49 for avoiding interference with an infusion tube TU to be fitted or inserted into an inlet opening 52 and an outlet opening 54 of the heating plate 40.

The electrical heater 38 heated up to a temperature of about 50 (° C.), for example, may be formed of a heating wire contained in a metal casing made of aluminum alloy or the like and electrically supported in an insulated state via an electrically insulating powder of inorganic or metal oxide, etc. Alternatively, the electrical heater 38 may be a heating wire embedded in a heat-resistant resin, or enclosed in a heat-resistant resin bag together with an insulating liquid. The plate material 46 may be a metal plate made of iron or aluminum alloy, or a heat-resistant resin plate.

The heating plate 40 is a rectangular plate formed of a metal with low heat conductivity, such as aluminum. As shown in the front view in FIG. 5, the rear view in FIG. 6, and the sectional view in FIG. 7, a front surface (one side) and a rear surface (the other side) are provided with a front-side tube fitting groove 50 and a rear-side tube fitting groove 60, respectively. The front-side tube fitting groove 50 and rear-side tube fitting groove 60 each have a U-shaped groove cross section, into which the infusion tube TU can be detachably inserted and which can closely fit to or face to the infusion tube TU. The heating plate 40 is preferably provided with a first heat-generating portion and a second heat-generating portion, which can be independently controlled to achieve control performance with a reduced likelihood of overshooting or hunting.

At the front surface of the heating plate 40, the front-side tube fitting groove 50 includes an inlet opening 52, an outlet opening 54, a basic groove 56, and shunting grooves 58a and 58b. The inlet opening 52 and the outlet opening 54 are open at one end surface and the other end surface, respectively, which correspond to the pair of short sides of the heating plate 40. The basic groove 56 is formed between the inlet opening 52 and the outlet opening 54 at a first length. The shunting grooves 58a and 58b shunt the basic groove 56 in a middle thereof so that the length between the inlet opening 52 and the outlet opening 54 can have a second length which is shorter than the first length. The front-side tube fitting groove 50 can receive the first length of the infusion tube TU as well as the second length of the infusion tube TU which is shorter than the first length.

Figure 5:
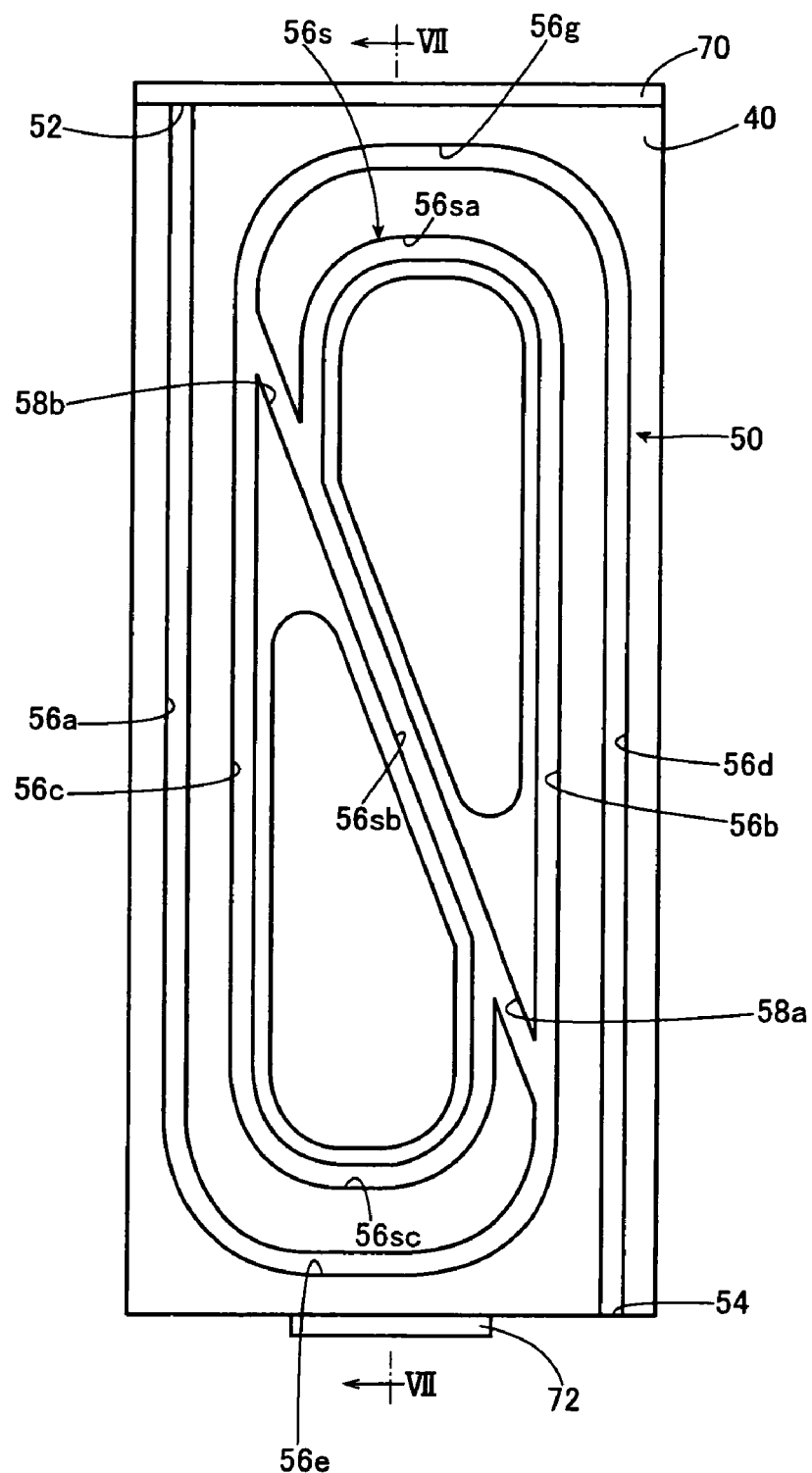
FIG. 5 is a front view showing a front of a heating plate to be detachably attached to a case body of the infusion fluid heating apparatus shown in FIG. 1.

As specifically shown in FIG. 5, the basic groove 56 includes a first straight groove 56a, a third straight groove 56c, a second straight groove 56b, and a fourth straight groove 56d arranged successively from side of the inlet opening 52 of the heating plate 40 in a width direction and are parallel to the longitudinal direction. The basic groove 56 further includes a semicircular first connection groove 56e which connects ends of the first straight groove 56a and the second straight groove 56b mutually at side of the outlet opening 54; an second S-shaped connection groove 56s which connects an end of the second straight groove 56b at side of the inlet opening 52 and an end of the third straight groove 56c at side of the outlet opening 54; and a third semicircular connection groove 56g which connects ends of the third straight groove 56c and the fourth straight groove 56d at side of the inlet opening 52. The total length of the straight grooves 56a, 56b, 56c and 56d, and the connection grooves 56e, 56s and 56g corresponds to the first length.

The second S-shaped connection groove 56s includes a semicircular curved portion 56sa, a diagonal straight portion 56sb, and a semicircular curved portion 56sc. One end of the curved portion 56sa is connected to an end of the second straight groove 56b at side of the inlet opening 52, and one end of the straight portion 56sb is connected to the other end of the curved portion 56sa. One end of the curved portion 56sc is connected to the other end of the straight portion 56sb, and the other end thereof is connected to an end of the third straight groove 56c at side of the outlet opening 54.

The shunting groove 58a shunts the basic groove 56 establishing a connection between a trailing end of the first semicircular connection 56e and the straight portion 56sb of the second S-shaped connection groove 56s. The shunting groove 58b also shunts the basic groove 56 establishing a connection between the straight portion 56sb of the second S-shaped connection groove 56s and a leading end of the third straight groove 56c. The shunting groove 58a, the straight portion 56sb of the second connection groove 56s, and the shunting portion 58b are formed in a straight line. A total length of the straight grooves 56a and 56d, the connection grooves 56e and 56g, the shunting groove 58a, the straight portion 56sb of the second connection groove 56s, and the shunting groove 58b corresponds to the second length. The second length is shorter than the first length by the amount determined by subtracting the total length of the shunting groove 58a, the straight portion 56sb of the second connection groove 56S, and the shunting groove 58b from that of the third straight groove 56c, the second straight groove 56b, and the second S-shaped connection groove 56s.

Figure 7:
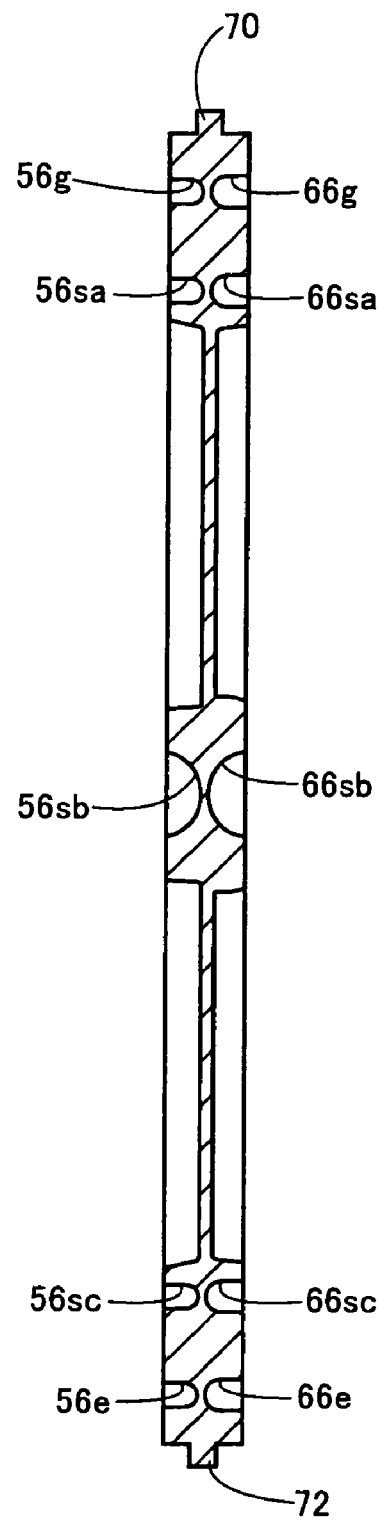
FIG. 7 is a VII-VII sectional view of FIG. 5 or 6, illustrating shape of a tube fitting groove formed on the heating plate equipped in the infusion fluid heating apparatus shown in FIG. 1.

At the rear surface of the heating plate 40, likewise the front-side tube fitting groove 50, a rear-side tube fitting groove 60 includes an inlet opening 62, an outlet opening 64, a basic groove 66, and shunting grooves 68a and 68b. The inlet opening 62 and the outlet opening 64 are open at one end surface and the other end surface, respectively, which correspond to the pair of short sides of the heating plate 40. The basic groove 66 is formed between the inlet opening 62 and the outlet opening 64 at a third length. The shunting grooves 68a and 68b shunt the basic groove 66 in a middle thereof so that the length between the inlet opening 62 and the outlet opening 64 can have a fourth length which is shorter than the third length. The rear-side tube fitting groove 60 can receive the third length of the infusion tube TU as well as the fourth length of the infusion tube TU which is shorter than the third length. As shown in FIG. 7, the rear-side tube fitting groove 60 has a sectional shape different from that of the front-side tube fitting groove 50, that is, a width dimension and a depth dimension of the former is selected to be larger than that of the latter. Here, the third length may be equal to the first length, and the fourth length may be equal to the second length.

Figure 6:
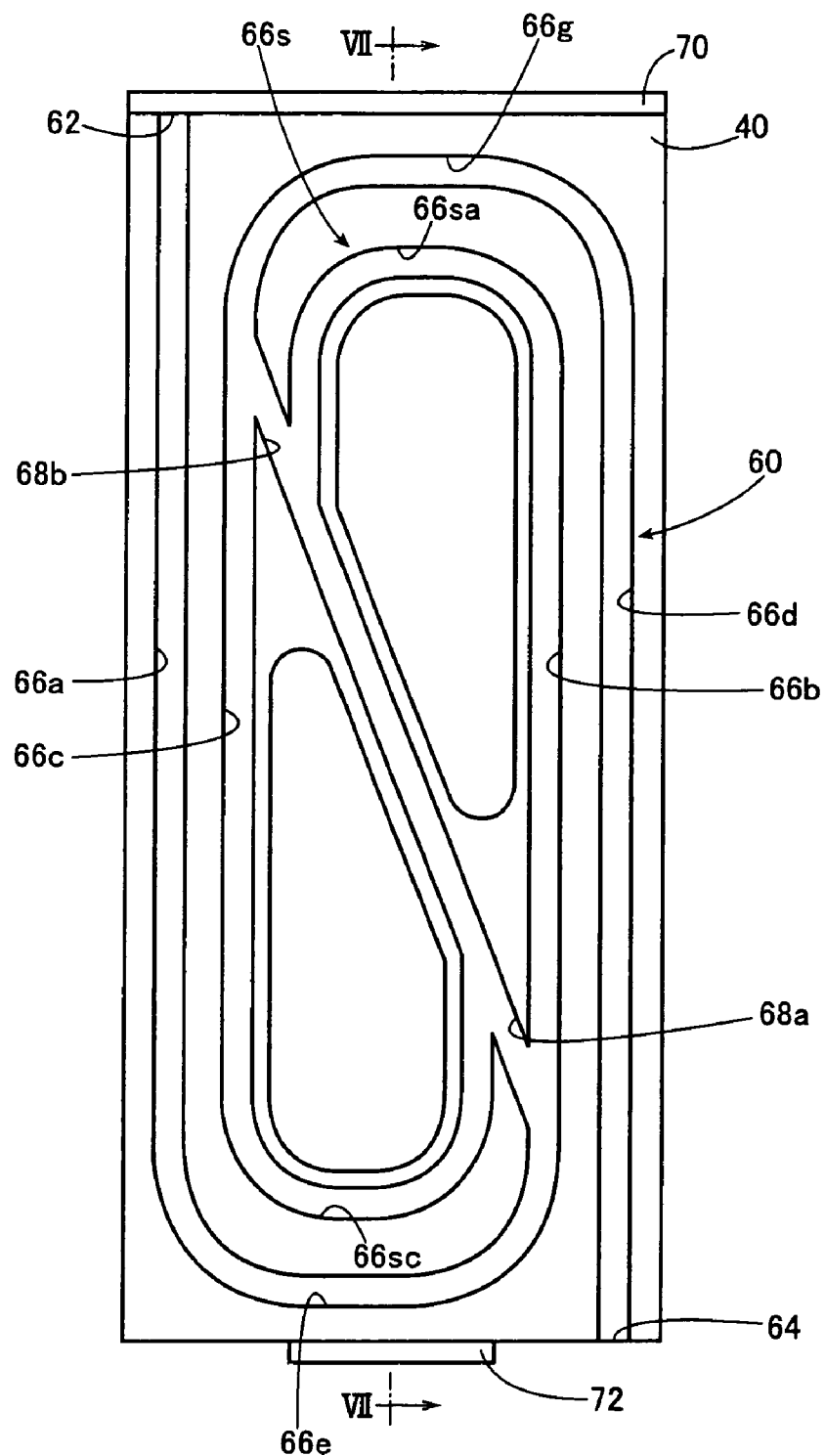
FIG. 6 is a rear view showing a rear of a heating plate to be detachably attached to the case body of the infusion fluid heating apparatus shown in FIG. 1.

As specifically shown in FIG. 6, the basic groove 66 includes a first straight groove 66a, a third straight groove 66c, a second straight groove 66b, and a fourth straight groove 66d arranged successively from side of the inlet opening 62 of the heating plate 40 in a width direction and are parallel to the longitudinal direction. The basic groove 66 further includes a semicircular first connection groove 66e which connects ends of the first straight groove 66a and the second straight groove 66b mutually at side of the outlet opening 64; an second S-shaped connection groove 66s which connects an end of the second straight groove 66b at side of the inlet opening 62 and an end of the third straight groove 66c at side of the outlet opening 64; and a third semicircular connection groove 66g which connects ends of the third straight groove 66c and the fourth straight groove 66d at side of the inlet opening 62. The total length of the straight grooves 66a, 66b, 66c and 66d, and the connection grooves 66e, 66s and 66g corresponds to the third length.

The second S-shaped connection groove 66s includes a semicircular curved portion 66sa, a diagonal straight portion 66sb, and a semicircular curved portion 66sc. One end of the curved portion 66sa is connected to an end of the second straight groove 66b at side of the inlet opening 62, and one end of the straight portion 66sb is connected to the other end of the curved portion 66sa. One end of the curved portion 66sc is connected to the other end of the straight portion 66sb, and the other end thereof is connected to an end of the third straight groove 66c at side of the outlet opening 64.

The shunting groove 68a shunts the basic groove 66 establishing a connection between a trailing end of the first semicircular connection 66e and the straight portion 66sb of the second S-shaped connection groove 66s. The shunting groove 68b also shunts the basic groove 66 establishing a connection between the straight portion 66sb of the second S-shaped connection groove 66s and a leading end of the third straight groove 66c. The shunting groove 68a, the straight portion 66sb of the second connection groove 66s, and the shunting portion 68b are formed in a straight line. A total length of the straight grooves 66a and 66d, the connection grooves 66e and 66g, the shunting groove 68a, the straight portion 66sb of the second connection groove 66s, and the shunting groove 68b corresponding to the fourth length. The fourth length is shorter than the third length by the amount determined by subtracting the total length of the shunting groove 68a, the straight portion 66sb of the second connection groove 66S, and the shunting groove 68b from that of the third straight groove 66c, the second straight groove 66b, and the second S-shaped connection groove 66s.

Figure 8:
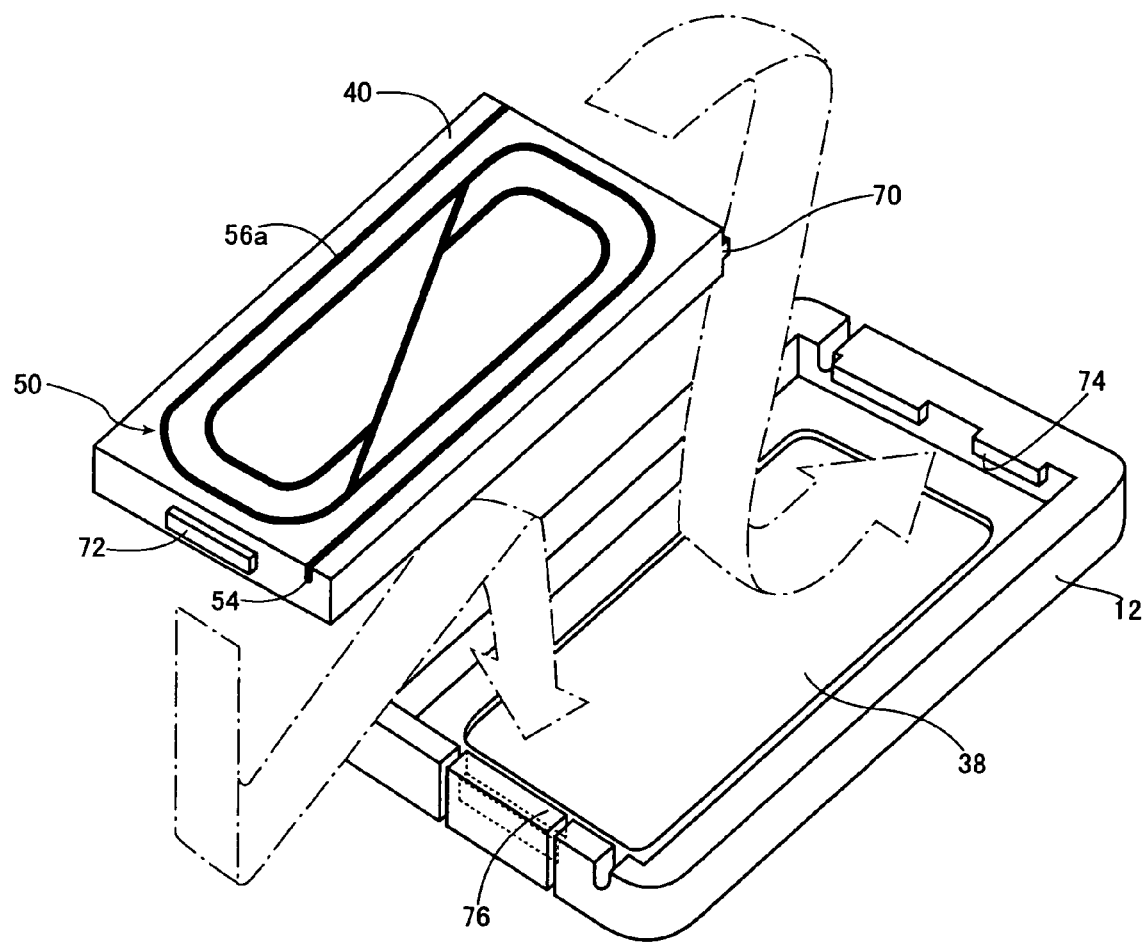
FIG. 8 is a perspective view illustrating structure for detachably fixing the heating plate equipped in the infusion fluid heating apparatus as shown FIG. 1.

As specifically shown in FIG. 8, both end surfaces of the heating plate 40 are provided with engaging projecting portions 70 and 72 projecting from the center in the thickness direction thereof. A portion corresponding to one of the paired short sides of the rectangular opening of the case body 12 is provided with a pair of fixing projections 74 which engages and fixes the engaging projecting portion 70. A portion corresponding to the other of the paired short sides is provided with a movable projecting portion 76 which can engage with the engaging projecting portion 72 and can be operated to move in a direction away from the engaging projecting portion 72. This structure enables the heating plate 40 to be fixed in the opening of the movable case body 12 as follows. With the engaging projecting portion 70 formed at one end of the heating plate 40 engaged with the fixing projection 74, the other end thereof is pressed into the case body 12, so that the engaging projecting portion 72 engages the projection 76. Meanwhile, the heating plate 40 can be removed from the movable case body 12 by operating the movable projecting portion 76 in a direction away from the heating plate 40 to disengage the movable projecting portion 76 from the engaging projecting portion 72. Such detachable attachment can be achieved on either surface of the heating plate 40.

An infusion bag B may be accommodated in a space of the case body 12 created by removal of the heating plate 40, so that an infusion fluid in the infusion bag B can be directly heated by the electrical heater 38.

Figure 9:
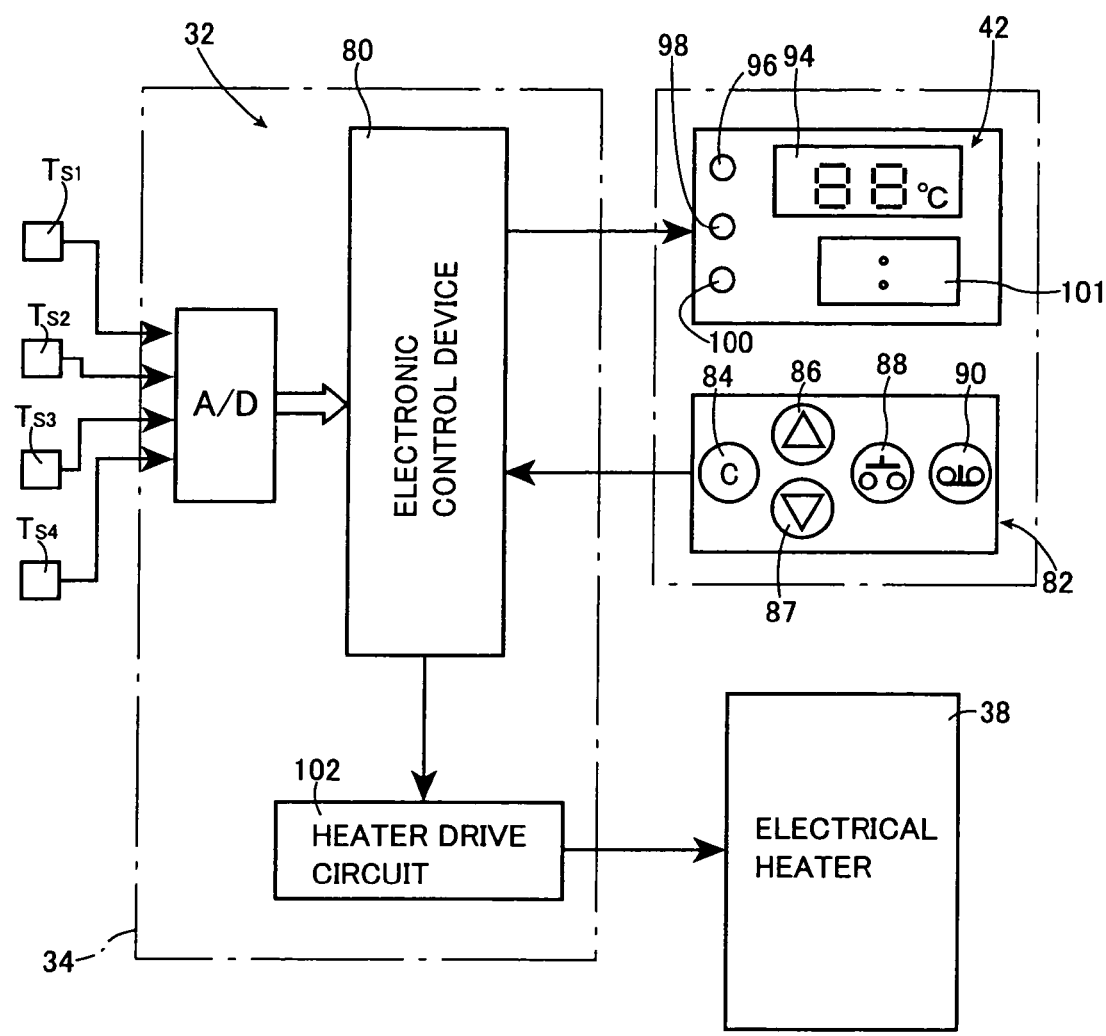
FIG. 9 is a circuit diagram illustrating an electronic control circuit equipped in the infusion fluid heating apparatus as shown in FIG. 1.

FIG. 9 is a block diagram illustrating the structure of an electronic control circuit which includes a temperature control unit 32 disposed on a first circuit substrate 34 and a display 42 disposed on the second circuit substrate 44. In FIG. 9, temperature sensors TS1, TS2, TS3 and TS4 each being formed by a thermistor, etc., detect the temperatures of the outlet of the infusion tube TU, the heating plate 40, and the first heat-generating portion and the second heat-generating portion of the electrical heater 38, and they supply signals indicating the detected temperatures to an electronic control device or electronic controller 80. An operation unit 82 includes a check operation switch 84, preset temperature changing switches 86 and 88, a start switch 89, and a stop switch 90, and it supplies signals indicating the operation of these switches to the electronic controller 80.

The electronic controller 80 processes input signals according to the prestored program to control lighting of a temperature display 94, an on-heating indicator 96, a warning indicator 98, a timer indicator 100, and an on-time display 101, which are included in the display 42. The electronic controller 80 also controls the heat generating amount of the electrical heater 38 through a heater drive circuit 102 so that an infusion fluid to be supplied to the living body reaches a preset target temperature, or that the temperature indicated by the temperature sensor TS1 is maintained about at the target temperature of 42° C., for example.

Further, the electronic controller 80 drives a temperature indicator 94 to indicate the measured temperature of the infusion fluid at the outlet. When the infusion fluid is overheated, the electronic controller 80 drives a sound generator (not shown) to generate an alarm, and the warning indicator 98 to emit light. The electronic controller 80 also drives the heating indicator 96 to emit light during operation of the electrical heater 38, and the timer indicator 100 to light up during setting of the timer.

The thus-constructed infusion fluid heating apparatus 10 is used to heat the infusion fluid to be supplied to the living body through an infusion tube TU connected to the infusion bag B, as shown in FIG. 1. When the lid 18 is open to expose the heating plate 40, the middle part of the infusion tube TU is inserted into the front-side tube fitting groove 50 or the rear-side tube fitting groove 60 formed on the heating plate 40.

Subsequently, with the lid 18 being closed, the infusion fluid in the infusion tube TU is heated via the heating plate 40 up to a preset temperature. Infusion tube TU generally used in actual medical field is made of polyvinyl chloride, for example. The thickness dimension, i.e., outer diameter, thereof falls in ranges of about 3 to 12 (mmφ), for example. There are a variety of products according to the standards of countries or manufacturers.

The infusion bag B and the infusion fluid heating apparatus 10 are hung from a stand (not shown). The infusion fluid contained in the infusion bag is heated up to a moderate temperature while it passes through the infusion tube TU. An injection needle (not shown) attached to the trailing end of the infusion tube TU is inserted into a vessel of a patient who is to receive the infusion. The liquid stored in the infusion bag B, such as blood, a nutrition liquid, or a liquid medicine is infused, through a drip tube connected to the infusion tube TU, a roller clamp, the infusion tube TU, and the injection needle, into a vessel in an arm or the like of the patient who receives the infusion.

As described above, according to the infusion fluid heating apparatus 10 of this embodiment, the front-side tube fitting groove 50 or the rear-side tube fitting groove 60 formed on one surface of the heating plate 40 has the inlet opening 52 or 62 and the outlet opening 54 or 64, which are open at the end surfaces of the heating plate 40. The groove receives the infusion tube TU in the first length between the inlet opening 52 or 62 and the outlet opening 54 or 64, and it also receives the infusion tube TU in the second length which is shorter than the first length. Thus, the tube fitting groove 50 or 60 uses the second length for a relatively short infusion tube TU, enabling to heat the tube appropriately and achieve high versatility. In addition, the tube fitting groove 50 or 60 uses the first length for the infusion bag B with the relatively long infusion tube TU, enabling to heat the tube appropriately and increase the maximum infusion fluid flow.

Further, according to the infusion fluid heating apparatus 10 of this embodiment, the front-side tube fitting groove 50 or the rear-side tube fitting groove 60 formed on the heating plate 40 has the inlet opening 52 or 62 and the outlet openings 54 or 64. The tube fitting groove 50 or 60 includes the basic groove 56 or 66 formed at the first length between the inlet opening 52 or 62 and the outlet opening 54 or 64, and the shunting grooves 58a and 58b or 68a and 68b which shunt the basic groove 56 or 66 in the middle so that the second length can be defined between the inlet opening 52 or 62 and the outlet opening 54 or 64. This enables the part of the basic groove 56 or 66 to both receive the first length of the infusion tube TU and the second length of the infusion tube TU. Thus, the heating plate 40 can be made compact.

Further, according to the infusion fluid heating apparatus 10 of this embodiment includes the case body 12 to which the heating plate 40 is detachably attached. The rear-side tube fitting groove 60 is formed on the other surface thereof, which corresponds to the second tube groove having the different sectional shape from the front-side tube fitting groove 50 formed on one surface of the heating plate 40. Thus, the infusion fluid heating apparatus 10 can heat the infusion tubes TU of different sectional shapes or diameter dimensions, thereby further improving versatility.

Further, according to the infusion fluid heating apparatus 10 of this embodiment, the rear-side tube fitting groove 60 corresponding to the second tube fitting groove, has the inlet opening 62 and the outlet opening 64 open at the end surfaces on the rear surface (other side) of the heating plate 40. The rear-side tube fitting groove 60 receives the infusion tube TU in the third length between the inlet opening 62 and the outlet opening 64, and it also receives the infusion tube TU using the third length which is shorter than the first length. As a result, on the other surface of the heating plate, the rear-side tube fitting groove 60 can use the fourth length for a relatively short infusion tube TU, capable of heating the tube appropriately and achieving high versatility. In addition, the rear-side tube fitting groove 60 can use the third length for the infusion bag with the long infusion tube TU, capable of heating the tube appropriately and increasing the maximum infusion fluid flow. Thus, higher versatility is achieved.

The case 20 of the infusion fluid heating apparatus 10 according to this embodiment includes the electrical heater 38 which closely fits the heating plate 40, the temperature sensor TS1, and the temperature control unit 32. The temperature sensor TS1 directly or indirectly detects the temperature of the infusion fluid in the infusion tube TU near the outlet opening 54. The temperature control unit 32 controls the heat generation amount at the electrical heater 38 so that the temperature detected by the temperature sensor TS1 coincides with the preset target temperature. This offers the advantage that any various type infusion fluid in the infusion bag can be introduced at the constant preset temperature.

Further, according to the infusion fluid heating apparatus 10 of this embodiment, the case 20 may be provided with the infusion bag containing the infusion fluid, in place of the heating plate 40. This renders the advantage that the infusion fluid can be heated even if the infusion tube TU is far shorter than the second length, provided that the volume of the bag B is relatively small.

While the preferred embodiment of the invention has been explained in detail based on the drawings, the invention is not limited thereto but may be embodied according to other embodiments thereof.

For example, in the above embodiment the front-side tube fitting groove 50 or the rear-side tube fitting groove 60 is formed in the pattern shown in FIG. 5 or 6 in the heating plate 40. However, the groove pattern is not limited to such mode, and the grooves can be formed in other various patterns.

Moreover, in the above heating plate 40, the front-side tube fitting groove 50 or the rear-side tube fitting groove 60 includes the basic groove 56 or 66 and the shunting grooves 58a and 58b or 68a and 68b. The basic groove 56 or 66 is formed at the first length between the inlet opening 52 or 62 and the outlet opening 54 or 64. The shunting grooves 58a and 58b or 68a and 68b shunt the basic groove 56 or 66 in the middle so that the second length is defined between the inlet opening 52 or 62 and the outlet opening 54 or 64. This enables the application of the part of the basic groove 56 or 66 to both cases of the first length of the infusion tube TU being inserted and the second length of the infusion tube TU being inserted. However, other groove pattern without inclusion of any such commonly applicable part is also available.

The electrical heater 38 of the above embodiment is provided with the first heat-generating portion and the second heat-generating portion, which can be independently controlled to achieve control performance with the reduced likelihood of overshooting or hunting. However, the electrical heater may have a single heat-generating portion.

In the infusion fluid heating apparatus 10 of the above embodiment, the single electrical heater 38 is placed on the rear surface of the heating plate 40. However, a second electrical heater 38 may be provided on the rear surface of the lid 18 in place of the plate material 46, to closely fit to the front surface of the heating plate 40.

The temperature sensor TS1 is provided at the outlet-side end in the circulation direction of the infusion fluid flowing through the infusion tube TU, but an additional temperature sensor may also be provided at the inlet-side end in the circulation direction of the fluid. Naturally, additional devices may also be provided, such as a device which generates an alarm upon air mixture in the infusion fluid, and a device which stops the circulation of the infusion fluid upon occurrence of problems. Furthermore, with respect to operation indication, not only the above display lamp 28 but also devices which indicate a room temperature, an infusion inlet-side temperature, a temperature setting, and the like may be provided appropriately as required.

Various modifications can be made without deviating from the scope of the invention, Although they are not given in every detail.

The invention claimed is:

1. An infusion fluid heating apparatus for pre-heating to a present temperature an infusion fluid to be supplied to a living body through an infusion tube, the infusion fluid heating apparatus comprising:
   a heating plate having a first surface and a second surface on an opposite side of the first surface, the heating plate including a first tube fitting groove formed on the first surface for receiving the infusion tube; and
   a case to which the heating plate is detachably attached,
   wherein a second tube fitting groove is formed on the second surface of the heating plate, the second tube fitting groove having a different sectional shape than a sectional shape of the first tube fitting groove, and
   the first tube fitting groove formed on the first surface of the heating plate includes a first portion for receiving the infusion tube and extending in a first length between an inlet opening and an outlet opening formed at respective end surfaces of the heating plate, and also includes a second portion for receiving the infusion tube and extending in a second length shorter than the first length.

2. The infusion fluid heating apparatus according to claim 1, wherein the first tube fitting groove includes a basic groove formed in the first length between the inlet opening and the outlet opening, and a shunting groove shunting the basic groove in a middle thereof so that the second length is defined between the inlet opening and the outlet opening.

3. The infusion fluid heating apparatus according to claim 2, wherein the second tube fitting groove includes a first portion for receiving the infusion tube and extending in a third length between the inlet opening and the outlet opening, and also includes a second portion for receiving the infusion tube and extending in a fourth length shorter than the third length.

4. The infusion fluid heating apparatus according to claim 3, wherein the case contains an electrical heater closely fitted to the heating plate, a temperature sensor that directly or indirectly detects a temperature of the infusion fluid in the infusion tube near the outlet opening, and a control unit that controls a heat generation amount of the electrical heater so that the temperature detected by the temperature sensor coincides with a preset target temperature.

5. The infusion fluid heating apparatus according to claim 4, wherein the case is provided with an infusion bag containing the infusion fluid, in place of the heating plate.

6. The infusion fluid heating apparatus according to claim 2, wherein the case contains an electrical heater closely fitted to the heating plate, a temperature sensor that directly or indirectly detects a temperature of the infusion fluid in the infusion tube near the outlet opening, and a control unit that controls a heat generation amount of the electrical heater so that the temperature detected by the temperature sensor coincides with a preset target temperature.

7. The infusion fluid heating apparatus according to claim 6, wherein the case is provided with an infusion bag containing the infusion fluid, in place of the heating plate.

8. The infusion fluid heating apparatus according to claim 1, wherein the second tube fitting groove includes a first portion for receiving the infusion tube and extending in a third length between the inlet opening and the outlet opening, and also includes a second portion for receiving the infusion tube and extending in a fourth length shorter than the third length.

9. The infusion fluid heating apparatus according to claim 8, wherein the case contains an electrical heater closely fitted to the heating plate, a temperature sensor that directly or indirectly detects a temperature of the infusion fluid in the infusion tube near the outlet opening, and a control unit that controls a heat generation amount of the electrical heater so that the temperature detected by the temperature sensor coincides with a preset target temperature.

10. The infusion fluid heating apparatus according to claim 9, wherein the case is provided with an infusion bag containing the infusion fluid, in place of the heating plate.

11. The infusion fluid heating apparatus according to claim 1, wherein the case contains an electrical heater closely fitted to the heating plate, a temperature sensor that directly or indirectly detects a temperature of the infusion fluid in the infusion tube near the outlet opening, and a control unit that controls a heat generation amount of the electrical heater so that the temperature detected by the temperature sensor coincides with a preset target temperature.

12. The infusion fluid heating apparatus according to claim 11, wherein the case is provided with an infusion bag containing the infusion fluid, in place of the heating plate.

* * * * *